United States Patent
Robertson

(10) Patent No.: US 8,919,849 B1
(45) Date of Patent: Dec. 30, 2014

(54) TRANSPORTABLE HYBRID OPERATING ROOM

(71) Applicant: AMoHS, Inc., Boulder, CO (US)

(72) Inventor: William G. Robertson, Covington, LA (US)

(73) Assignee: AMoHS, Inc., Boulder, CO (US)

( * ) Notice: Subject to any disclaimer, the term of this patent is extended or adjusted under 35 U.S.C. 154(b) by 0 days.

(21) Appl. No.: 14/144,984

(22) Filed: Dec. 31, 2013

Related U.S. Application Data

(60) Provisional application No. 61/747,710, filed on Dec. 31, 2012.

(51) Int. Cl.
 *A61G 3/00* (2006.01)
(52) U.S. Cl.
 CPC ........................................ *A61G 3/001* (2013.01)
 USPC ....................................................... 296/24.38
(58) Field of Classification Search
 USPC ....................................................... 296/24.38
 See application file for complete search history.

(56) References Cited

U.S. PATENT DOCUMENTS

| | | | | |
|---|---|---|---|---|
| 4,302,913 A | | 12/1981 | Schwartz et al. | |
| 4,402,442 A | * | 9/1983 | Martino | 224/324 |
| 4,738,369 A | * | 4/1988 | Desjardins | 211/113 |
| 4,915,435 A | | 4/1990 | Levine | |
| 6,039,377 A | * | 3/2000 | Eberspacher | 296/24.38 |
| 6,170,102 B1 | * | 1/2001 | Kreuzer | 5/601 |
| 6,601,985 B1 | * | 8/2003 | Jesurun et al. | 362/572 |
| 7,794,001 B2 | * | 9/2010 | Blackwell et al. | 296/24.38 |
| 8,198,616 B2 | * | 6/2012 | Rees | 250/516.1 |
| 2011/0147563 A1 | * | 6/2011 | Metelski | 248/610 |

FOREIGN PATENT DOCUMENTS

WO 2013060503 A1 5/2013

* cited by examiner

*Primary Examiner* — Lori L Lyjak
(74) *Attorney, Agent, or Firm* — Downs Rachlin Martin PLLC

(57) ABSTRACT

A transportable hybrid operating room (THOR). The THOR includes a transportable unit with an interior for use in the imaging of and performance of surgery on a patient, the interior including a ceiling. The THOR also includes a support assembly positioned above the unit for supporting equipment used in conjunction with such imaging and surgery so that the equipment extends downwardly from the ceiling into the interior. The support assembly is designed to support a load of at least 3,500 pounds.

14 Claims, 6 Drawing Sheets

TRANSPORTABLE HYBRID OPERATING ROOM

RELATED APPLICATION DATA

This application is a non-provisional of U.S. Provisional Patent Application Ser. No. 61/747,710, filed Dec. 31, 2012, entitled "Transportable Hybrid Operating Room," which application is incorporated by reference herein in its entirety.

FIELD OF THE INVENTION

The present invention generally relates to the field of mobile healthcare units. In particular, the present invention is directed to a transportable hybrid operating room.

BACKGROUND

Recently, hospitals have come to recognize the benefit of combining in one space imaging systems (e.g., X-ray) and operating rooms for invasive surgery. These spaces, which have come to be known as hybrid operating rooms ("ORs"), require extensive modification of existing healthcare facilities. Hybrid ORs require substantially more free space than conventional ORs because imaging equipment must be accommodated along with conventional OR equipment such as operating tables. Further, because imaging equipment is heavy, the internal structure in the space housing a conventional OR is frequently not designed to support the weight of such imaging equipment.

Healthcare facilities often build new structures to house a hybrid OR. Because a significant planning and capital investment is required to build such structures, it often takes a number of years to construct a hybrid OR. Renovating existing healthcare space to house a hybrid OR can sometimes be completed faster than building a new structure to house a hybrid OR, and in some cases at lower cost. Regardless of whether space for a hybrid OR is newly constructed or renovated, a need often exists for such space for a number of years before construction is completed. Existing mobile surgery units are not believed to satisfy the various requirements for hybrid ORs, in part because they lack the structure required to suspend from the ceiling the heavy equipment used in a hybrid OR. Indeed, known mobile surgery units typically cannot be used to suspend more than about 500 pounds from the ceiling of the unit, at least while still staying within other design parameters (e.g., snow loading) for the unit.

SUMMARY OF THE DISCLOSURE

In one implementation, the present disclosure is directed to a hybrid operating room for performing imaging and surgery. The hybrid operating room comprises a housing including a roof and an interior having a first size that is large enough to function as a hybrid operating room, said housing including a central unit, a first side section coupled to said central unit and a second side section coupled to said central unit opposite said first side section, said central unit, first side section and second side section together defining said interior; and a support assembly for supporting equipment suspended within said interior of said housing, said support assembly comprising a plurality of support columns and a support structure positioned above said roof of said housing and supported by said support columns, said support structure having a weight and said support columns extending between said support structure and a surface on which said housing is positioned so that the weight of said support structure and any equipment attached thereto is transmitted to the surface.

In another implementation, the present disclosure is directed to a hybrid operating room for performing imaging and surgery. The hybrid operating room comprises a structure including a roof and an interior having a first size that is large enough to function as a hybrid operating room; and a support assembly for use in suspending equipment used in a hybrid operating room within said interior of said housing, said support assembly comprising a plurality of support columns and a support structure positioned above said roof of said structure and supported by said support columns, wherein said support assembly is capable of supporting a load of at least 3,500 pounds.

In yet another implementation, the present disclosure is directed a method of using equipment in a hybrid operating room. The method comprises assembling a team of healthcare professionals in the interior of a transportable unit, the interior defining a hybrid operating room, the interior having a ceiling; supporting equipment used in imaging of a patient and performing surgery on a patient from a support assembly positioned above the unit so that the equipment extends downwardly from the ceiling into the interior; and performing imaging of and surgery on a patient using the equipment.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Figure 1:
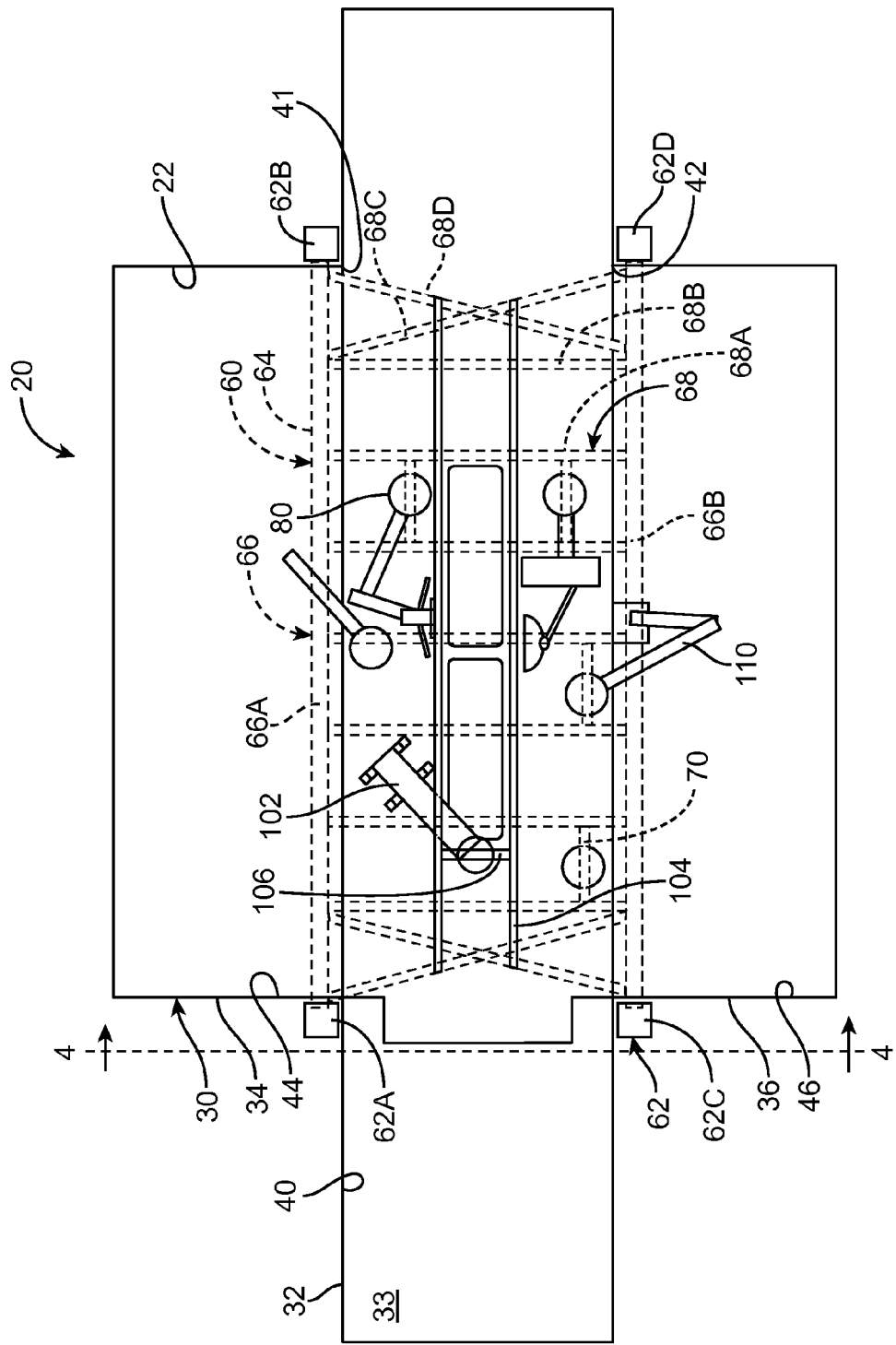
FIG. 1 is a top view of a transportable hybrid operating room ("THOR"), with certain equipment used in a hybrid OR illustrated in solid view and a support assembly illustrated in phantom view, a portion of the roof and interior ceiling of the THOR being removed to facilitate depiction of such equipment.

Referring to FIG. 1, the present disclosure relates to a THOR 20 having an interior 22 in which body imaging, e.g., using a C-arm X-ray machine, and invasive surgical procedures, e.g., cardiac catherization, may be performed in the open space defined by the interior. Interior 22, in one embodiment, is one free space that is entirely open, i.e., there are no walls or columns invading the interior. As discussed more below, interior 22 is typically large enough to satisfy contemporary requirements for a hybrid operating room, and so in this regard includes 800 square feet or more, 1,000 square feet in one embodiment.

THOR 20 includes a housing 30 having, in one embodiment, a central unit 32 with a top surface 33, a first side section 34 and a second, opposing, side section 36. Central unit 32 may, for example, be designed to be transported from one location to another on public and private roadways (in some cases with special permits), either using a separate power unit (not shown), or with its own power source (not shown). In one embodiment, central unit 32 is a wheeled trailer of the sort pulled by a separate "tractor" (not shown) on roads and highways. In other embodiments, central unit 32 may lack wheels and be transported on a flatbed truck, by helicopter or otherwise to a desired location. In this regard, ISO containers and other known structures may be used as central unit 32. The length and width of central unit 32 will vary depending on intended application, although in one implementation the central unit is 60 feet long and 12 feet wide. The length and width of side sections 34 and 36 may also be chosen in view of the intended application, although in one implementation the side sections are 30 feet long and 12 feet wide. In this implementation of central unit 32 and side sections 34 and 36, interior 22 encloses approximately 1,000 square feet. The amount of space enclosed by interior 22 should, more generally, be selected to satisfy whatever regulations, standards of care, insurance requirements, Medicare requirements and other criteria are in place at the time and location where THOR 20 is used. In some cases this space will be less than 1,000 square feet and in other cases more than 1,000 square feet.

Central unit 32 includes an interior 40 that is in communication via side openings 41 and 42 with interior 44 of first side section 34 and interior 46 of second side section 36, so as to define interior 22. In this regard, the side portions (not shown) of side sections 34 and 36 proximate central unit 32 are open so as to permit communication, via side openings 41 and 42, among interiors 40, 44 and 46 so as to define interior 22.

In one embodiment, side sections 34 and 36 may be separate sections that are bolted to or otherwise attached to central unit 32 after moving the central unit to a desired location. With such embodiment, side sections 34 and 36 may be manufactured off-site and trucked or otherwise transported to the location where THOR 20 is installed, or may be built at such location. In another embodiment, side sections 34 and 36 may be mounted to central unit 32 so as to slide in and out relative to the central unit from a position fully nested in the central unit to a fully expanded position as indicated in FIG. 1. With respect to this latter embodiment, it will generally be necessary to remove any equipment suspended from the ceiling of THOR 22 to permit side sections 34 and 36 to be nested. An example of a mobile surgery unit having such expandable and retractable sides is described and shown in U.S. Pat. No. 4,915,435 to Levine, which is incorporated herein by reference in its entirety, particularly those portions discussing equipment and construction required for invasive surgery and those portions relating to the expandable sides. In one embodiment, central section 32 may be designed and constructed so that it may be transported on roadways as a single unit. In another embodiment, central section 32, together with side sections 34 and 36, may be designed and constructed so that they may be transported on roadways as a single unit. In yet another embodiment, each of side sections 34 and 36 may be designed and constructed so that they may be transported on roadways as a single unit.

To permit invasive surgery to be performed in THOR 20, the latter is designed and constructed to satisfy governmental regulations, health insurance and Medicare reimbursement standards, healthcare industry requirements, and other relevant requirements as relates to invasive surgery, as the intended use of the THOR dictates. Those of ordinary skill in the art will understand and appreciate the design and construction details required to satisfy such requirements, as demonstrated by the existence of mobile surgery units of the sort sold by AMoHS of Boulder, Colo. See www.amohs.com. Such requirements include, without limitation, minimum square footages for interior 22, pre/post op areas with minimum square footages around each gurney in such areas, certain minimum air filtration, air pressure and air exchange requirements, and positively and negatively charged rooms to minimize airborne contamination. Other requirements include equipment used to perform invasive surgical procedures, e.g., endoscopes, anesthesia machines, gas supplies for such machines, electrosurgery generators, insufflators, cameras, surgical tools, and video displays. Other more prosaic items such as a locking narcotics cabinet, a janitor's sink. ADA-compliant bathrooms, and clean and soiled linen spaces may also be provided.

Equipment used in connection with body imaging such as C-arm X-ray equipment of the type sold by Siemens AG and Koninklijke Philips Electronics N.V. is routinely used in hybrid operating rooms and so may be used in THOR 20. Other body imaging equipment such as ultra-sound, MRI and other X-ray equipment may also be included in THOR 20. Because of size constraints in a hybrid operating room, even one as large as 1000 square feet, arising from the large number of healthcare professionals (e.g., up to 18 professionals) working together, it is desirable to minimize the amount of equipment positioned on the floor of the operating room. In response to this condition, THOR 20 may be constructed so that as much equipment as possible is suspended to extend downwardly from the ceiling of the THOR.

The construction of typical trailers, ISO containers and other structures that may be used as central unit 32 generally lack the structure necessary to support heavy objects from the ceiling of such structures. Accordingly, it is difficult to satisfy the objective of supporting equipment used in hybrid operating rooms from the ceiling of structures usable as central unit 32 of THOR 20.

Referring now to FIGS. 1-5, to address this limitation, THOR 20 includes a support assembly 60 from which equipment used in the THOR is suspended. Support assembly 60, in one embodiment, includes four support columns 62, i.e., columns 62A, 62B, 62C and 62D and a support structure 64 supported by columns 62. Columns 62 should have a design, construction and size adequate to support structure 64. In one embodiment, columns 62 are steel I-beams with a cross-sectional height of 15 inches. In another embodiment, columns 62 are reinforced concrete structures having a square cross section, with each side measuring about 24 inches. Columns 62 may have yet other size, design and construction depending on the loads to be carried by support assembly 60, as those of ordinary skill in the art will readily appreciate.

Figure 6:
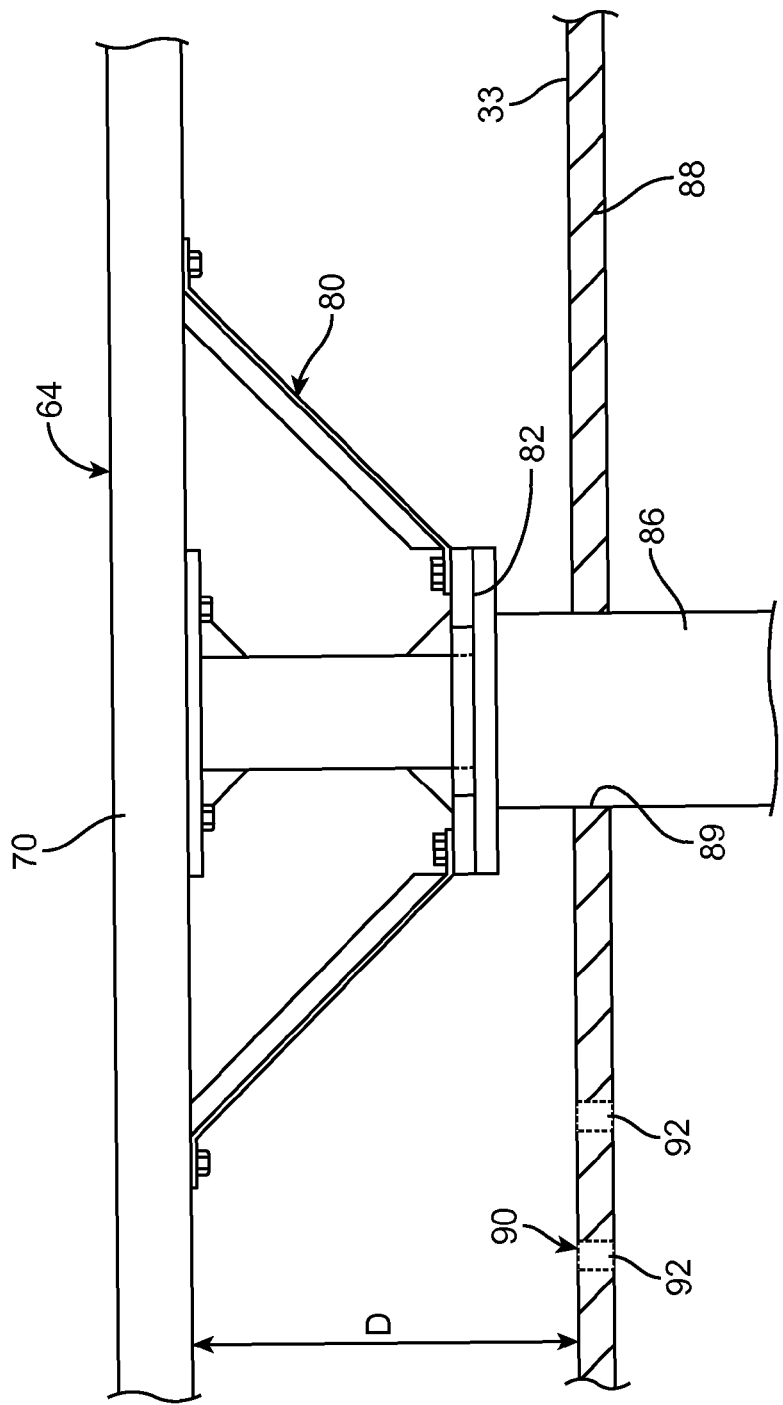
FIG. 6 is a side view of an attachment assembly used in the THOR to couple the support assembly with a piece of equipment used in the THOR.

In use, columns 62 may be positioned on a pad or other structure (not shown) underneath THOR 20 designed to accommodate the load the columns will carry. Alternatively, columns 62 may rest on reinforced portions of the floor or frame (not shown) of central section 32 or side sections 34 and 36. In such embodiment, it may be desirable to provide support columns 65 (shown in dotted view in FIG. 3 to indicate their optional nature), extending between the underside of central section 32 and/or side sections 34 and 36 and a pad or other structure (not shown) underneath THOR 20. Columns 65, in some embodiments, have a length selected so that the bottom of support structure 64 is spaced a distance D (FIG. 6) from top surface 33 of central section 32. In some embodiments, distance D ranges from 3-6 inches. It may be desirable, in some situations, to jack up central section 32 after THOR 20 is suitably positioned relative to support assembly 60 to achieve this distance D spacing. In some implementations, columns 65 will not be provided when columns 62 are constructed to rest on a pad or other structure underneath THOR 20. An another alternative, columns may be received within the periphery of central section 32 and/or side sections 34 and 36, through openings (not shown) provided in such sections so as to rest on a pad underneath THOR 32 or on reinforced floor portions of the THOR, using columns 65 with respect to this latter alternative, as desired. In some implementations, it may be desirable to attach sway bracing to columns 62 extending away from the columns and mounted to the surface on which the columns rest or attached to other structure. Support structure 60 may be constructed in several sections, e.g., four sections, moved to THOR 20, lifted into place and then fully assembled, or may be assembled in "stick-built" fashion, i.e., one member at a time.

In one embodiment, columns 62 are spaced apart so that central unit 32 fits in between with a gap (not shown), e.g., 6-15 inches, sufficient to allow the central unit to be maneuvered into place between the columns. In such embodiment, columns 62 may be positioned just in front and just behind side sections 34 and 36, as best illustrated in FIG. 1, e.g., spaced 6-15 inches in front of or behind the side sections. Alternatively, as noted above, columns 62 may be positioned within the periphery of central section 32 and/or side sections 34 and 36. In any event, it will generally be desirable to position columns 62 so as to provide as much open space as possible in interior 22.

Support structure 64, in one embodiment, comprises primary members 66A and 66B and cross members 68, e.g., members 68A and 68B, extending between and connected to the primary members. If desired, several of cross members, e.g., members 68C and 68D, may be positioned in a crisscross pattern to increase rigidity of support structure 64. Further, in some applications it may be desirable to provide connectors 70 extending between adjacent cross members 68. Members 66, 68 and 70 are connected together by welding, through the use of fasteners such as bolts or with other techniques for fastening. In one embodiment, primary members 66 are implemented using steel I-beams that are 30 feet long and have a cross-sectional height of 24 inches, and cross members are implemented using steel I-beams having a cross-sectional height of 40 inches. To reduce vibration, to support heavier loads and for other reasons, it may be desirable in certain applications to increase the height of primary members 66 to 30 inches or more. Concerning the overall dimensions of support structure 64, the structure should be large enough to extend over or near locations where equipment used in THOR 20 will be located, as discussed more below. In one embodiment, support structure is about 30 feet along, as measured along primary members 66 and about 15 feet wide, as measured along cross members 68.

Materials used to construct support structure 64, the dimensions of such materials, and overall size of the support structure should be selected with reference to the weight of equipment to be supported by the support structure, acceptable vibration of the support structure and other factors. In one embodiment, support structure 64 is designed and constructed to support a 40,000 pound static (i.e., dead weight) load. In another embodiment, support structure 64 is designed and constructed to support a 25,000 pound static load. In yet another embodiment, support structure 64 is designed and constructed to support a 3,500 pound static load. In other embodiments, support structure 64 is designed and constructed to support a static load in the 3,500-55,000 pound range. In addition to supporting these static loads, support structure 64 should also be designed and constructed to support dynamic or moment-arm loads that are 3-4 times the static loads discussed above.

Figure 2:
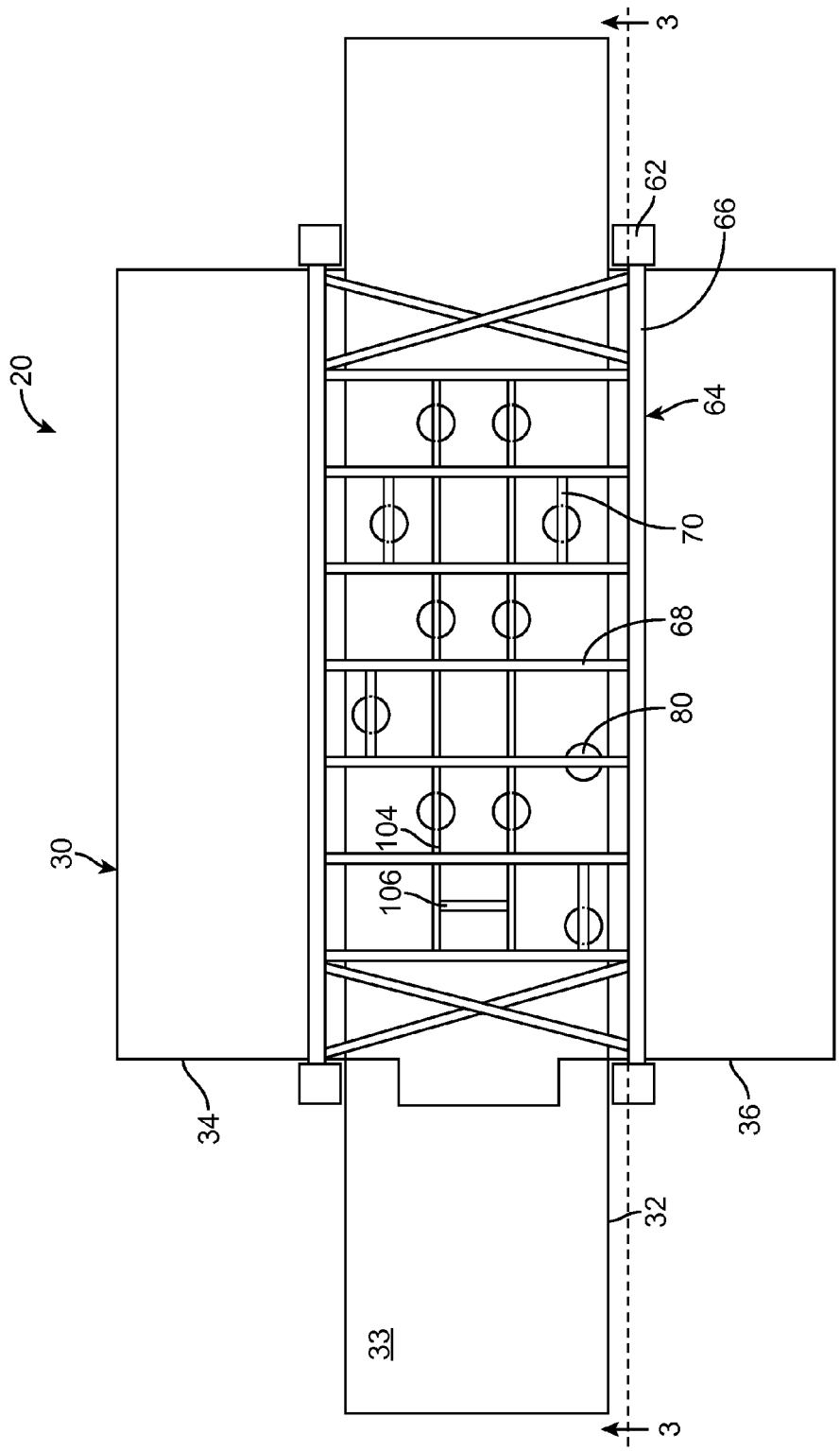
FIG. 2 is a top view similar to FIG. 1, except that the support assembly is illustrated in solid view and equipment positioned inside the THOR is not illustrated.

Referring to FIGS. 1-4 and 6, equipment used in THOR 20 may be suspended from support structure 64 using various load-transferring structures. In one embodiment, an attachment assembly 80 (see FIG. 6) is connected to cross members 68 or connectors 70, as best illustrated in FIGS. 1 and 2. Central unit 32 may include a ceiling 88 with an opening 89 through which attachment assembly 80 extends. In one embodiment, the space in opening 89 between attachment assembly 80 and ceiling 88 is filled with a gap-filling material, such as a rubber gasket or expandable foam, that prevents air infiltration around the attachment assembly and keeps out dirt and other debris. Attachment assembly 80 terminates at a lower end at mounting face 82, to which mounting structure 86 for equipment used in THOR 20 may be attached. Alternatively, ceiling 88 may be constructed to include a framing assembly 90 (FIG. 6) made up of a plurality of elongate framing members 92 that are designed, when installed, to permit equipment to be suspended at desired locations along the length of the members. Typically, framing assembly 90 is made from metal, although other materials may also be used. Framing assembly 90 may be positioned proximate ceiling 88 (e.g., embedded in the ceiling, in one embodiment). In one embodiment, framing members 92 extend parallel to one another and perpendicular to the long dimension of central unit 32 in spaced relation to one another (e.g., 1 foot apart) along the long dimension. One commercial embodiment of framing assembly 90 is sold by Unistrut International Corporation under the trademark UNISTRUT®. Framing assembly 90 may be secured to support structure 64 with connectors 92 (FIG. 3) that extend between the framing assembly and primary members 66, cross members 68 and connectors 70, as desired.

Body imaging equipment 100, e.g., C-arm X-ray device 102, used in THOR 20 may be mounted in a fixed location to support structure 64 via attachment assembly 80. Alternatively, body imaging equipment may be mounted for sliding movement along or across support structure 64. To effectuate such mounting, a rail track 104 and dolly 106 that slides along the rail track may be provided on the inside surface of ceiling 88. In the embodiment of THOR 20 illustrated in FIGS. 1-3, the long dimension of rail track 104 extends parallel to the long dimension of primary members 66 and is attached to support structure 64 using mounting structure known to those skilled in the art, including without limitation attachment assemblies 80. When metal framing assembly 90 is used, rail track 104 may be suspended from the ceiling 88 using the framing assembly. Imaging equipment 100 is attached to dolly 106 for movement along rail track 104.

Discussing further equipment used in THOR 20, one or more boom arms 110 may be attached to support structure 64 via attachment assemblies 80 or framing assembly 90. Boom arms 110 may support various equipment used in connection with body imaging and invasive surgery, including video monitors 112, surgical lights 114, and other devices not shown, including an X-ray shield, a carrier with multiple shelves for supporting items used in a hybrid operating room such as surgical instruments, endoscopes, electrosurgery generators, cameras, insufflators, and a panel for providing anesthesia gases and electrical outlets. Anesthesia machines may be connected to such panels. In some cases, it may be desirable to connect multiple pieces of equipment to one attachment assembly 80, e.g., a carrier and surgical lights. As a consequence of supporting equipment used in THOR 20 from support structure 64, the need for carts for housing equipment used in body imaging and surgery is minimized. Minimizing the use of carts can be beneficial since it makes the floor of THOR 20 less cluttered, which is desirable given the number of healthcare professional who often work in a hybrid operating room.

Regarding other equipment used in THOR 20, in some implementations it will be desirable to provide a first table 120 for supporting a patient during invasive surgery and a second table 122 for supporting a patient during body imaging. Optionally, a column 123 (FIGS. 3 and 4) may be provided for supporting second table 122 so that the weight of the second table is transmitted to the surface on which housing 30 rests. In other implementations, just one table is used, typically table 122, which would generally be positioned close to the longitudinal mid-point of interior 40 of central section 32. As discussed above, all other equipment necessary or desirable for body imaging and invasive surgery is also provided in THOR 20, whether suspended from support structure 64, positioned in carts (not shown), attached to walls of the THOR or otherwise provided.

Figure 3:
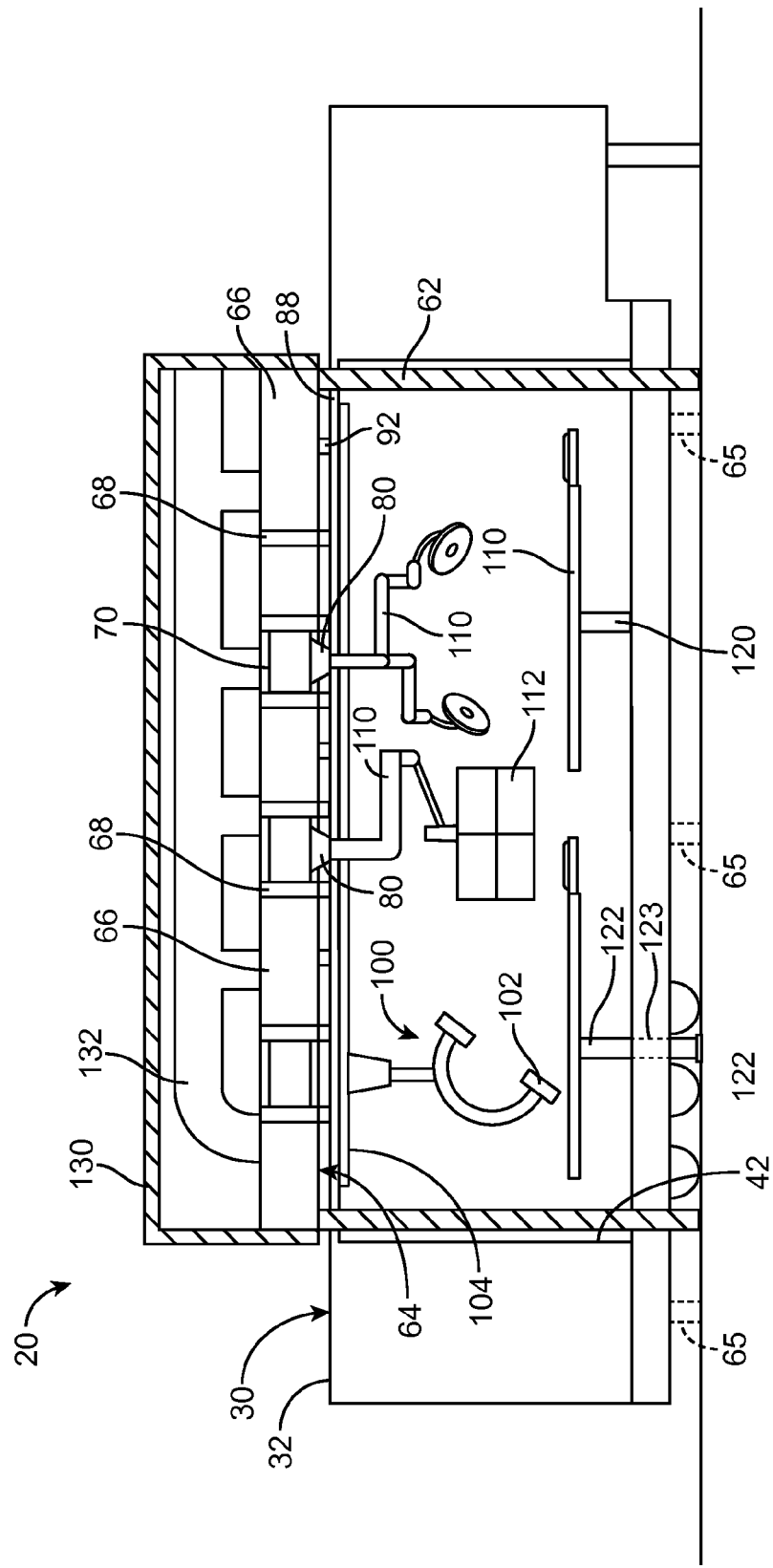
FIG. 3 is a cross-sectional side view of the THOR taken along line 3-3 in FIG. 2.
Figure 4:
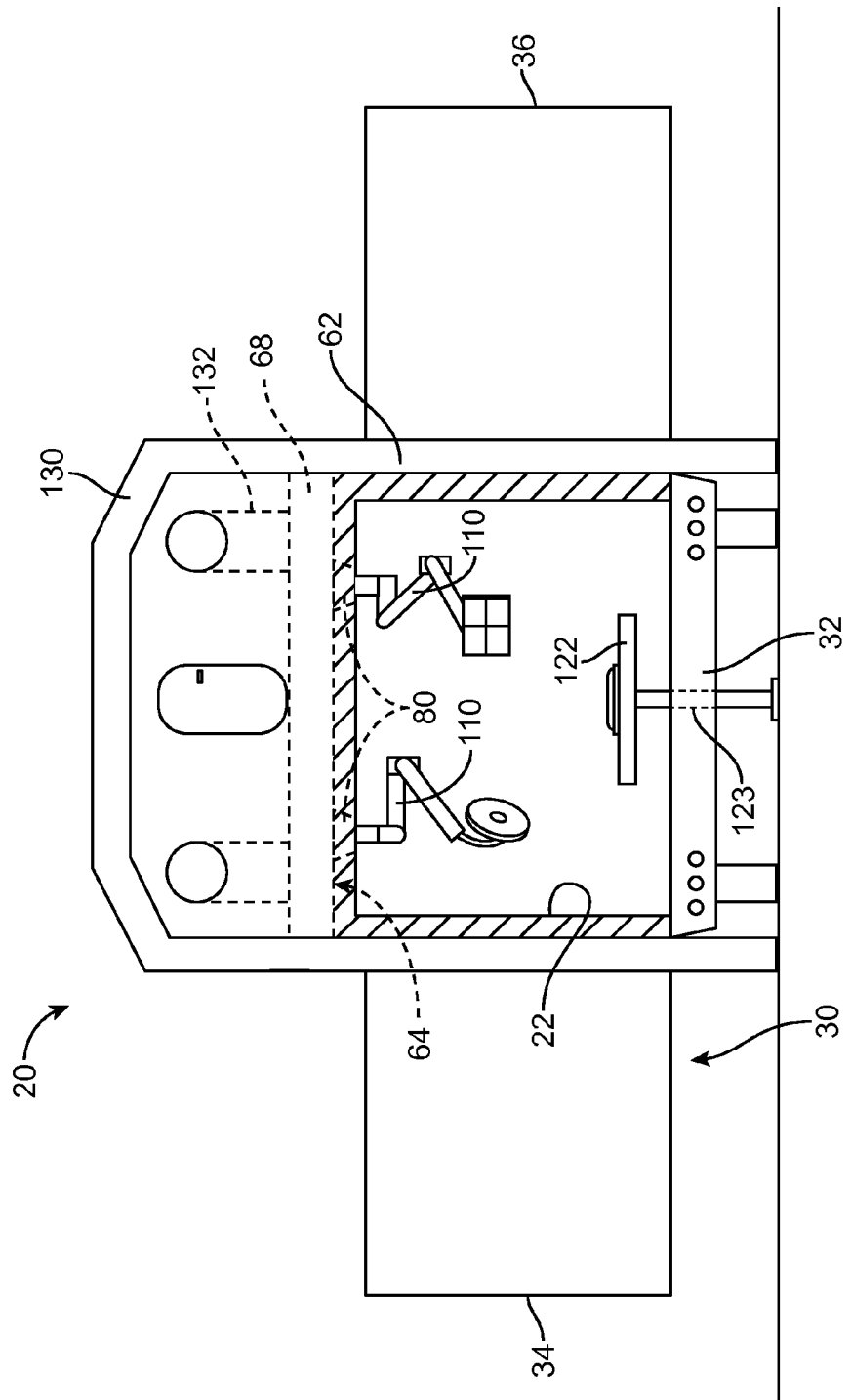
FIG. 4 is a end view of the THOR taken along line 4-4 in FIG. 1, with only some of the equipment inside the THOR being shown in FIG. 1 and with certain portions of the THOR being shown in phantom view.
Figure 5:
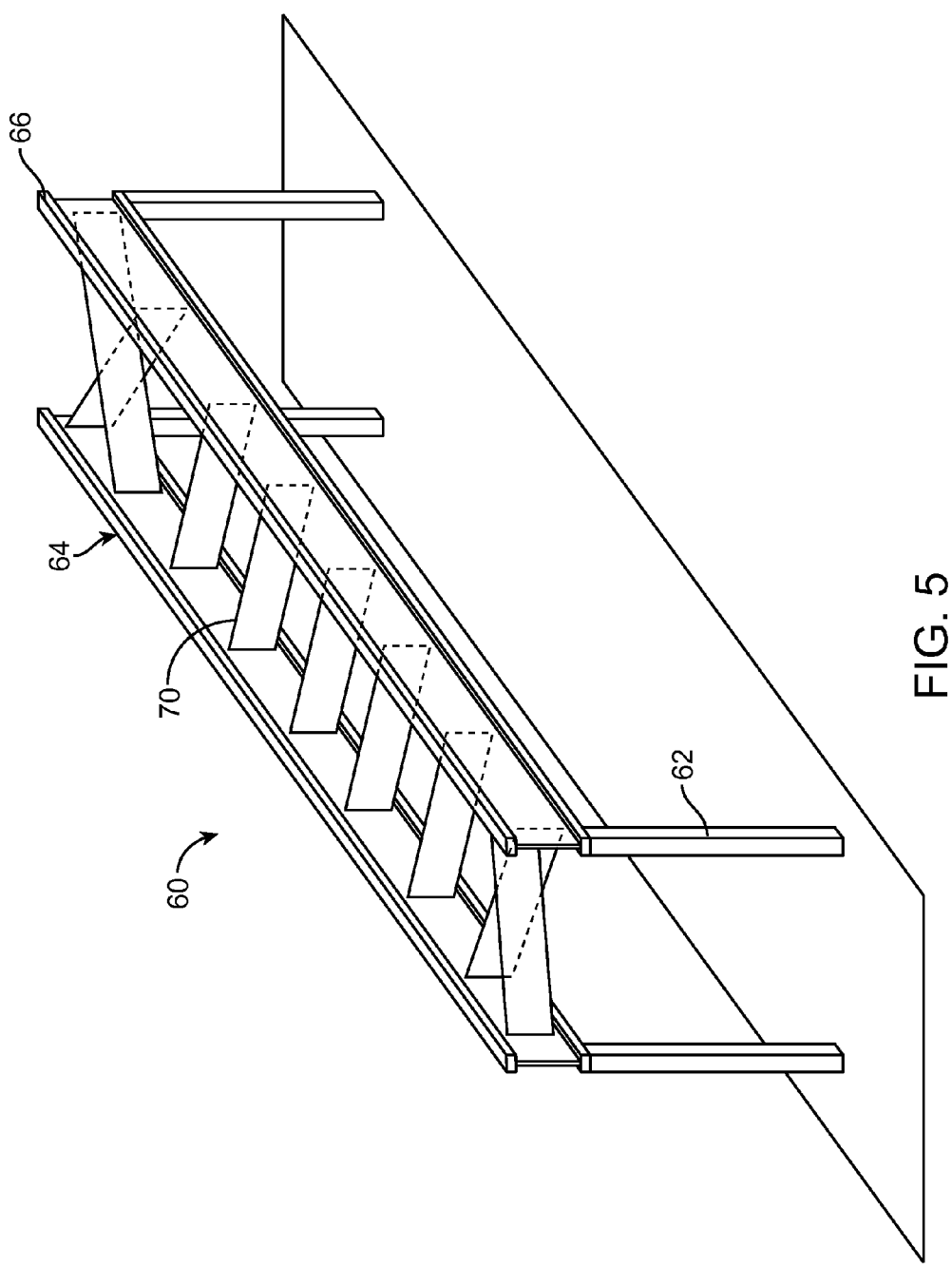
FIG. 5 is a perspective view of the support assembly of the THOR.

Referring to FIGS. 3 and 4, THOR 20 may, in some implementations, include a roof structure 130 covering support structure 64. Typically, roof structure 130 is designed and constructed to provide a weatherproof seal around support structure 64, including protecting the top surface 33 of central section 32 from exposure to the elements. Roof structure may be sized, if desired, to accommodate ductwork 132 for HVAC systems (not shown) used to control air temperature, pressure and quality in interior 22.

Support structure 60 has been described above as used in connection with housing 30 having a central section 32 and opposing side sections 34 and 36. It is to be appreciated, however, that support structure 60 may also be used in connection with just a central section 32 without side sections 34 and 36, or with just one side section 34 or 36. More generally, support structure 60 may be used with any structure having an interior 22 for use as a hybrid OR, including a "bricks and mortar" healthcare facility. In this regard, during new construction or renovation of a structure housing a hybrid OR, support structure 60 could be positioned on top of the structure on columns 62 (previously installed) using a crane or other device. Alternatively, Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A hybrid operating room for performing imaging and surgery, comprising:
    a housing including a roof and an interior having a first size that is large enough to function as a hybrid operating room, said housing including a central unit, a first side section coupled to said central unit and a second side section coupled to said central unit opposite said first side section, said central unit, first side section and second side section together defining said interior; and
    a support assembly for supporting equipment suspended within said interior of said housing, said support assembly comprising a plurality of support columns and a support structure positioned above said roof of said housing and supported by said support columns, said support structure having a weight and said support columns extending between said support structure and a surface on which said housing is positioned so that the weight of said support structure and any equipment attached thereto is transmitted to the surface.

2. A hybrid operating room according to claim 1, further including a plurality of attachment assemblies for connecting equipment used in a hybrid operating room with said support assembly so that said equipment may be suspended in said interior.

3. A hybrid operating room according to claim 1, wherein said central unit is sized and configured to be transported as a single unit on roadways.

4. A hybrid operating room according to claim 1, wherein said central unit, said first side section and said second side section are sized and configured to be transported as a single unit on roadways.

5. A hybrid operating room according to claim 1, wherein said support assembly is capable of supporting a load in the 3,500-55,000 pound range.

6. A hybrid operating room according to claim 5, wherein said support assembly is capable of supporting a load of at least 25,000 pounds.

7. A hybrid operating room according to claim 5, wherein said support assembly is capable of supporting a load of at least 3,500 pounds.

8. A hybrid operating room according to claim 1, further including at least one attachment assembly for connecting equipment used in a hybrid operating room with said support structure such that said equipment is suspended within the interior.

9. A hybrid operating room for performing imaging and surgery, comprising:
    a structure including a roof and an interior having a first size that is large enough to function as a hybrid operating room; and
    a support assembly for use in suspending equipment used in a hybrid operating room within said interior of said housing, said support assembly comprising a plurality of support columns and a support structure positioned above said roof of said structure and supported by said support columns, wherein said support assembly is capable of supporting a load of at least 3,500 pounds.

10. A hybrid operating room according to claim 9, wherein said support assembly is capable of supporting a load of at least 25,000 pounds.

11. A hybrid operating room according to claim 9, further wherein said interior is defined, in part, by a ceiling, and said structure includes a framing assembly proximate said ceiling that connects equipment used in a hybrid operating room with said support structure.

12. A hybrid operating room according to claim 9, further wherein said interior is defined, in part, by a ceiling, and said structure includes an attachment assembly proximate said ceiling that connects equipment used in a hybrid operating room with said support structure.

13. A method of using equipment in a hybrid operating room, comprising:
    assembling a team of healthcare professionals in the interior of a transportable unit, the interior defining a hybrid operating room, the interior having a ceiling;
    supporting equipment used in imaging of a patient and performing surgery on a patient from a support assembly positioned above the unit so that the equipment extends downwardly from the ceiling into the interior; and
    performing imaging of and surgery on a patient using the equipment.

14. A method according to claim 13, further including the step of moving the equipment within the interior of the unit in connection with said performing step.

* * * * *